(12) United States Patent
Buelow et al.

(10) Patent No.: US 11,024,028 B2
(45) Date of Patent: Jun. 1, 2021

(54) DEVICE AND METHOD FOR QUALITY ASSESSMENT OF MEDICAL IMAGE DATASETS

(71) Applicant: KONINKLIJKE PHILIPS N.V., Eindhoven (NL)

(72) Inventors: Thomas Buelow, Grosshansdorf (DE); Stewart Young, Hamburg (DE); Tanja Nordhoff, Hamburg (DE); Tim Philipp Harder, Ahrensburg (DE); Jan-Hendrik Buhk, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 124 days.

(21) Appl. No.: 16/339,053

(22) PCT Filed: Oct. 25, 2017

(86) PCT No.: PCT/EP2017/077307
§ 371 (c)(1),
(2) Date: Apr. 3, 2019

(87) PCT Pub. No.: WO2018/077949
PCT Pub. Date: May 3, 2018

(65) Prior Publication Data
US 2019/0244353 A1    Aug. 8, 2019

(30) Foreign Application Priority Data
Oct. 25, 2016  (EP) ..................................... 16195419

(51) Int. Cl.
*G06T 7/00*  (2017.01)
*G16H 30/40*  (2018.01)
(Continued)

(52) U.S. Cl.
CPC ............ *G06T 7/0014* (2013.01); *A61B 5/055* (2013.01); *A61B 6/032* (2013.01); *A61B 6/501* (2013.01);
(Continued)

(58) Field of Classification Search
CPC ........................................... G06T 2207/30016
See application file for complete search history.

(56) References Cited

U.S. PATENT DOCUMENTS 5,572,125 A * 11/1996 Dunkel .............. G01R 33/3875
324/307
9,747,702 B2 * 8/2017 Heismann .............. A61B 5/055
(Continued)

FOREIGN PATENT DOCUMENTS

WO     2012012768      1/2012

*Primary Examiner* — Iman K Kholdebarin
(74) *Attorney, Agent, or Firm* — Larry Liberchuk

(57) ABSTRACT

The present invention relates to a device and method for quality assessment of medical image datasets. To enable an automatic quality assessment of medical image datasets to identify potential errors or deviations that may be avoided in future imaging operations, the device comprises an image input (21) for obtaining medical image datasets together with respective acquisition information, each medical image dataset being acquired by scanning a field of view, FOV, of an examination object and the respective acquisition information representing information related to the acquisition of the respective medical image dataset; an image analysis unit (22) for comparing the FOV of an obtained medical image dataset with a reference FOV and for determining difference information indicating deviations of the FOV from the reference FOV; a correlation unit (23) for determining correlation information indicating correlations between the difference information determined for a plurality of obtained medical image datasets and the respective acquisition infor-
(Continued)

mation; and an output unit (24) for issuing the determined correlation information.

15 Claims, 3 Drawing Sheets

(51) Int. Cl.
    *A61B 5/055*     (2006.01)
    *G16H 40/63*     (2018.01)
    *A61B 6/00*     (2006.01)
    *G16H 40/20*     (2018.01)
    *A61B 6/03*     (2006.01)

(52) U.S. Cl.
    CPC ........... *A61B 6/5258* (2013.01); *G16H 30/40* (2018.01); *G16H 40/20* (2018.01); *G16H 40/63* (2018.01); *G06T 2207/10081* (2013.01); *G06T 2207/30016* (2013.01); *G06T 2207/30168* (2013.01)

(56) References Cited

U.S. PATENT DOCUMENTS

| | | |
|---|---|---|
| 2002/0032377 A1* | 3/2002 | Thesen ............ G01R 33/56509 600/419 |
| 2007/0147579 A1 | 6/2007 | De Man |
| 2009/0034812 A1 | 2/2009 | Nowinski |
| 2009/0041325 A1 | 2/2009 | Luo |
| 2011/0110572 A1 | 5/2011 | Guehring |
| 2011/0229005 A1 | 9/2011 | Den Harder |
| 2011/0246521 A1 | 10/2011 | Luo |
| 2012/0051608 A1* | 3/2012 | Avinash .................... G06T 7/11 382/128 |
| 2012/0114206 A1* | 5/2012 | Avinash ................. A61B 6/463 382/131 |
| 2013/0058545 A1 | 3/2013 | Pearson |
| 2014/0072192 A1 | 3/2014 | Reiner |
| 2014/0169652 A1 | 6/2014 | Torbjoern |
| 2016/0110584 A1* | 4/2016 | Remiszewski ..... G06K 9/00127 382/133 |

* cited by examiner

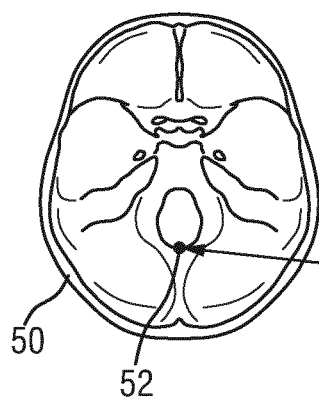 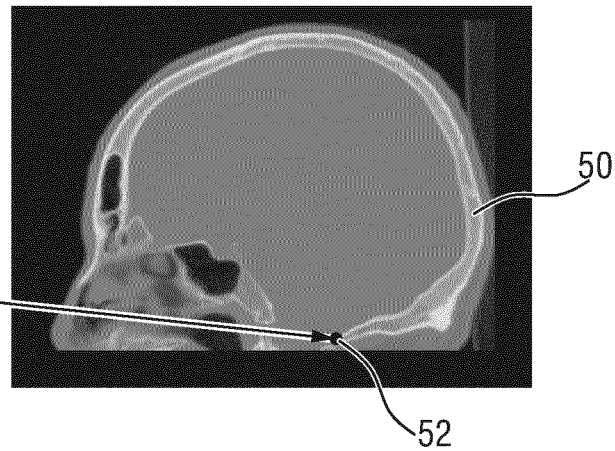
FIG.3A  FIG.3B
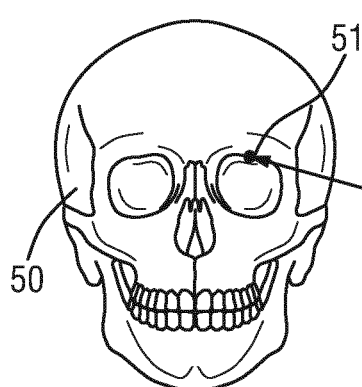 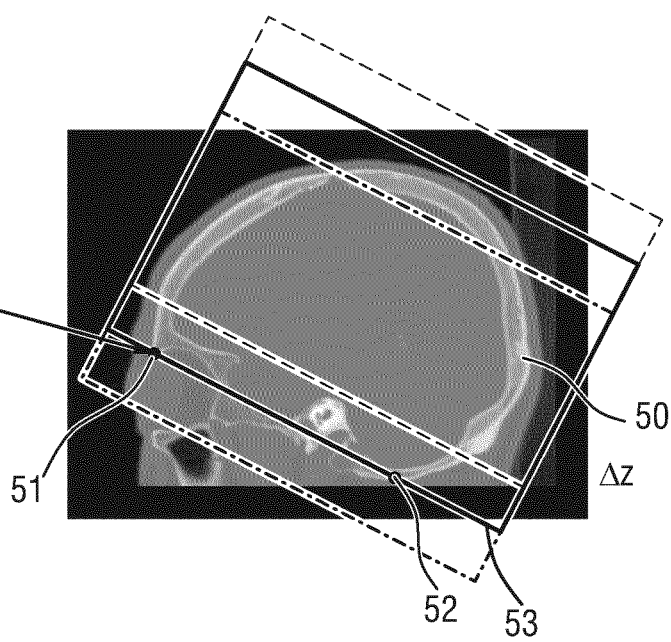
FIG.3C  FIG.3D

DEVICE AND METHOD FOR QUALITY ASSESSMENT OF MEDICAL IMAGE DATASETS

CROSS REFERENCE TO RELATED APPLICATIONS

This application is the U.S. National Phase application under 35 U.S.C. § 371 of International Application No. PCT/EP2017/077307, filed Oct. 25, 2017, published as WO 2018/077949 on May 3, 2018, which claims the benefit of European Patent Application Number 16195419.3 filed Oct. 25, 2016. These applications are hereby incorporated by reference herein.

FIELD OF THE INVENTION

The present invention relates to a device and method for quality assessment of medical image datasets. Further, the present invention relates to an imaging system.

BACKGROUND OF THE INVENTION

When performing CT scans of the brain, it is important to avoid inclusion of the eyes in the field of view (FOV) since the eye-lens is radio-sensitive. Radiation-induced damage to the eye-lens accumulates and can lead to cataracts. Also when scanning other parts of a patient's body, such as the abdomen, it is preferred not to include the genitals, in particular of a young patient, in the FOV if not needed. Similar precautionary measures may be advisable when performing medical imaging by use of another imaging modality than CT, e.g. in X-ray imaging or MR imaging.

While it is, for instance, easy to retrospectively identify whether the eyes are inside or outside the FOV, identification of specific errors/deviations of individual images does not, on its own, yield sufficient information on remedies for potential image quality issues.

SUMMARY OF THE INVENTION

It is an object of the present invention to provide a device and method that retrospectively allows an automatic quality assessment of medical image datasets to identify potential errors or deviations that may be avoided in future imaging operations. It is a further object of the present invention to provide a corresponding imaging system.

In a first aspect of the present invention a device for quality assessment of medical image datasets is presented comprising an image input for obtaining medical image datasets together with respective acquisition information, each medical image dataset being acquired by scanning a field of view, FOV, of an examination object and the respective acquisition information representing information related to the acquisition of the respective medical image dataset;

an image analysis unit for comparing the FOV of an obtained medical image dataset with a reference FOV and for determining difference information indicating deviations of the FOV from the reference FOV;

a correlation unit for determining correlation information indicating correlations between the difference information determined for a plurality of obtained medical image datasets and the respective acquisition information; and an output unit for issuing the determined correlation information.

In a further aspect of the present invention an imaging system is presented comprising an image acquisition system for acquiring medical image datasets of examination objects, and a device as disclosed herein for quality assessment of acquired medical image datasets.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

In general, it requires the accumulation of statistical evidence regarding the nature of the errors being made on an aggregated basis to provide a basis for decision-making regarding improvement actions. The present invention is hence based on the idea to automatically and retrospectively assess a number of image datasets to obtain correlation information showing potential errors and their sources so that improvements can be suggested to avoid errors in future imaging operations.

There are various options to determine the reference FOV and the image analysis unit may be configured accordingly. In one embodiment the reference FOV is determined from the analyzed medical image dataset itself. For instance, as provided according to another embodiment, the FOV may be determined by use of anatomical landmarks, such as recognizable anatomical structures (like bones, branches of vessels, etc.) within the obtained medical image dataset.

In another embodiment the reference FOV may be determined such that a predetermined anatomical region, in particular predetermined one or more sensitive organs, are excluded from the reference FOV. For instance, as mentioned above, it may be desired in a CT head scan to exclude the eyes from the scan.

Generally, various types of medical image datasets may be assessed by the present invention. The invention is particularly useful for CT image datasets, in particular of a human head, wherein said predetermined anatomical region are the eyes and said anatomical landmarks are the left and right supra orbital ridges and the opisthion of the occipital bone.

In still another embodiment the reference FOV may be determined from a database, in particular an anatomical atlas, based on said medical image dataset. Hence, based on the kind of medical image dataset, e.g. the information that it is a CT scan of the head, the database is accessed and a corresponding reference FOV for said kind of medical image dataset is taken from the database. The information which kind of image dataset is given may be explicitly specified in the dataset, e.g. as metadata provided along with the dataset, or may be determined automatically from the medical image dataset, e.g. by analyzing the contained image information).

In a preferred embodiment said image analysis unit is configured to determine difference information indicating deviations of the FOV from the reference FOV with respect to a predetermined condition, in particular a predetermined anatomical region. The predetermined condition may e.g. be specified by the instruction which FOV to scan or may be given through a general guideline with respect to the FOV. For instance, the predetermined condition may indicate the size and the limits of the FOV and/or which anatomical objects to include and/or exclude.

The image analysis unit may be configured in an embodiment to determine first if an obtained medical image dataset complies with a predetermined condition, in particular if it contains a predetermined anatomical region, and to compare the FOV of an obtained medical image dataset with a reference FOV and to determine difference information for an obtained medical image dataset only if it has been determined that the obtained medical image dataset complies with a predetermined condition. Thus, if the condition is not fulfilled, e.g. if—in the above mentioned example—the eyes are not included in the FOV, the medical image dataset is not further analyzed to save time and processing power.

Different kinds of difference information may be determined according to various embodiments of the disclosed device and method. For instance, in one embodiment the image analysis unit may be configured to determine difference information comprising translational information indicating deviations in size and/or one or more borders of the FOV of an obtained medical image dataset with respect to a reference FOV. In another embodiment the image analysis unit may be configured to determine difference information comprising rotational information indicating deviations of the FOV of an obtained medical image dataset with respect to a reference FOV in one or more rotational directions around one or more different rotational axes. In still another embodiment the image analysis unit may be configured to determine difference information comprising presence information indicating the extent of presence of a predetermined anatomical region, in particular one or more sensitive organs, in the FOV of an obtained medical image dataset. The kind of difference information that shall be determined may depend on the kind of medical image datasets and/or the important conditions that shall be met for said kind of medical image datasets. Hence, the user may e.g. determine in advance which difference information to obtain, or it may be automatically determined, e.g. based on a guideline, which difference information to determine.

According to another embodiment the acquisition information comprises at least one of temporal information indicating the time, in particular the day of the week and the time of day, of the acquisition of the respective medical image dataset, object information indicating the condition of the imaged examination object, position information indicating the position of the examination object with respect to an imaging device by which the respective medical image dataset has been acquired, and operator information about the operator indicating the operator who carried out the acquisition of respective medical image dataset.

Some or all of this information may be useful in the desired quality assessment and may be used to determine appropriate and useful correlation information to guide future acquisitions of image datasets and avoid possible errors.

BRIEF DESCRIPTION OF THE DRAWINGS

These and other aspects of the invention will be apparent from and elucidated with reference to the embodiment(s) described hereinafter. In the following drawings

FIGS. 3A-3D show different views and slice images of a skull illustrating landmarks defining the optimal lower scan plane of a brain CT scan;

DETAILED DESCRIPTION OF THE INVENTION

Figure 1:
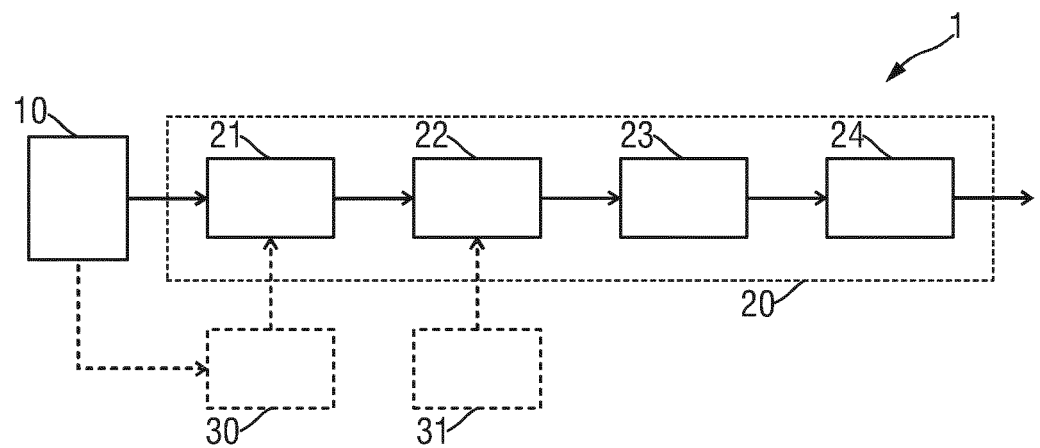
FIG. 1 shows a schematic diagram of a system and device according to the present invention.

FIG. 1 shows a schematic diagram of a system 1 and a device 20 for quality assessment of medical image datasets according to the present invention. The system 1 comprises an image acquisition system 10 for acquiring medical image datasets of examination objects, and the device 20 for quality assessment of acquired medical image datasets. The image acquisition system 10 may e.g. be a CT scanner that is configured to acquire a CT image dataset of an examination object, e.g. a patient or part of a patient, e.g. of the head, the torso, or the abdomen. In other embodiment the image acquisition system 10 may be an MR scanner for acquiring an MR image dataset of a patient or part of a patient.

The device 20 comprises an image input 21 for obtaining medical image datasets together with respective acquisition information, each medical image dataset being acquired by scanning a field of view, FOV, of the examination object and the respective acquisition information representing information related to the acquisition of the respective medical image dataset. The image input may e.g. be an interface that is able to access an image database 30, e.g. of a hospital, which stores a large number of image datasets acquired over time by use of the same or different operators, for a plurality of examination objects, and with the same or different image acquisition system (e.g. the same CT imaging scanner 10 or with different CT imaging scanners).

The device 20 further comprises an image analysis unit 22 for comparing the FOV of an obtained medical image dataset with a reference FOV and for determining difference information indicating deviations of the FOV from the reference FOV. For instance, two or more CT image datasets of the head of patients are analyzed to check if and which errors have occurred and if there are any correlations with respect to one or more of the operator, the time of the day, the weekday, the CT scanner, etc. Thus, in this example a reference FOV is obtained, e.g. from an optional reference database 31, which may also be part of a hospital's database or which may be available in an anatomical atlas e.g. in the cloud or on a particular server.

The device 20 further comprises a correlation unit 23 for determining correlation information indicating correlations between the difference information determined for a plurality of obtained medical image datasets and the respective acquisition information. The correlation information may e.g. indicate that a particular operator often makes the same error (e.g. uses a too small or too large FOV or a misplaced FOV or misplaces the scanned part of the patient's body) or that the same error is often occurring on the same day (e.g. Monday morning) or that the same scanner often shows the same error. An error may also be that not an entire organ of interest is in the FOV or than an organ is not correctly oriented as e.g. prescribed by a corresponding guideline (which may be important for enabling diagnostics), which is relevant not only for modalities that rely on ionizing radiation but also e.g. for MR imaging.

The determined correlation information is then issued by an output unit 24, which may comprise a data interface for transmitting the correlation to some other entity (e.g. a central computer of the hospital or the computer of a quality department or a doctor's computer). The output unit 24 may also comprise a display for directly displaying the correlation information, e.g. in the form of recommendations, statistics, charts, text information describing the content of the correlation information, etc.

The device 20 may generally be implemented in hard- and/or software, e.g. as a processor, computer or application program ("app") running on a user device, such as a smartphone, laptop, computer, etc., that is programmed accordingly. Further, the device 20 may be configured in the form of appropriate circuitry that is designed to carry out the steps of the method in accordance with the present invention. The device 20 may be integrally formed together with the image acquisition system 10, e.g. may be formed on the computer that is controlling the acquisition modules of the image acquisition system 10. In other embodiments, however, the image acquisition system 10 and the device 20 are separate entities that may be connected for providing image datasets from the image acquisition system 10 to the device 20. The image acquisition system 10 may alternatively not be connected with the device 20 but with an image database from which the device 20 obtains the image datasets to be analyzed.

Such an analysis may be made a regular or irregular intervals, e.g. once a month or once a year. In one embodiment, only image datasets for the same object of examination, e.g. the same anatomical region (e.g. the head), and/or from the same image acquisition system 10 are analyzed. In other embodiments, the analysis is made for image datasets for different objects of examination and/or for different image acquisition systems.

In an exemplary implementation of the device 20 an automatic image analysis is made by the image analysis unit 22 to identify whether the eyes are inside or outside the FOV of a brain CT scan. For images with at least part of the eyes within the FOV, the image analysis unit 22 detects the optimal FOV (i.e. a reference FOV) for this scan, e.g. from a guideline or database or anatomical imaging atlas. The image analysis unit 22 then compares the optimal FOV with the actual FOV of the brain CT scan. The correlation unit 23 then links identified quality deficiencies of an image with the root-cause for this deficiency to generate correlation information and, preferably, known remedies for the deficiency. The same analysis is applied to a large database (e.g., brain CT data in a PACS) to generate cumulative correlation information about the overall quality and specific improvement opportunities.

Figure 2:
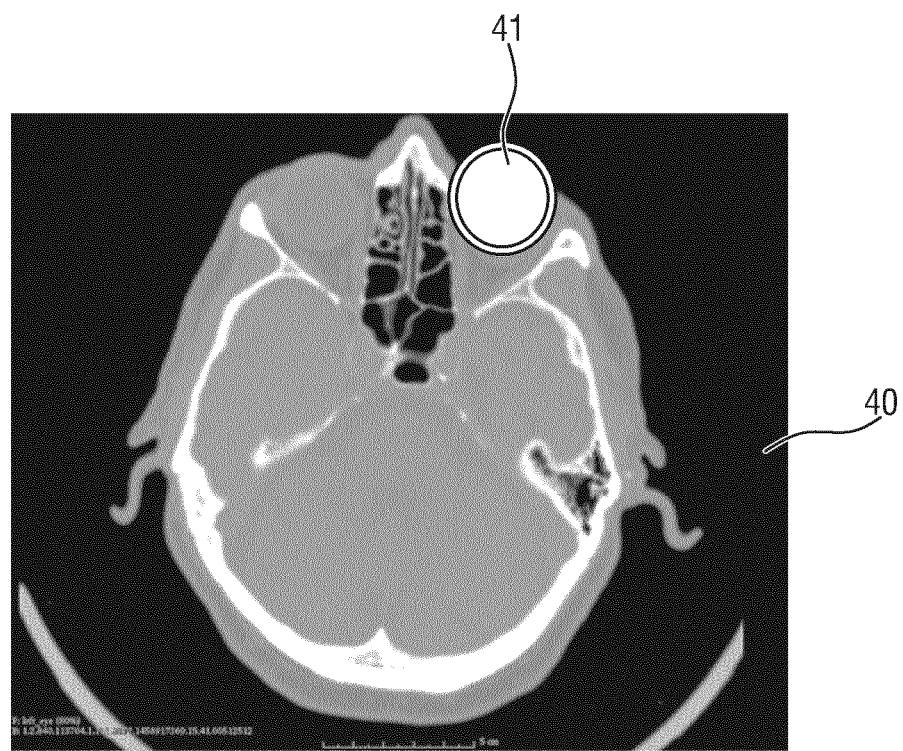
FIG. 2 shows an axial slice image of a brain CT scan with overlay of eye-probability map.

Various image analysis methods exist e.g. for the identification of eyes in the FOV. A preferred embodiment involves mapping of CT scans to a probabilistic anatomic atlas. For each voxel in the image, the likelihood of the voxel representing part of the eyes is given then as illustrated in FIG. 2 that shows an axial slice image 40 of a brain CT scan with overlay of an eye-probability map 41. Based on the location of regions with high eye-likelihood (within or outside the FOV), images are labelled as "eyes in image" or "eyes not in image".

By detection of landmarks the optimal (reference) FOV can be identified. This is illustrated in FIGS. 3A-3D showing different views and slice images of a skull 50 illustrating landmarks 51, 52 defining the optimal lower scan plane 53 of a brain CT scan. According to guidelines and clinical practice the lowest slice of the scan should intersect with the opisthion of the occipital bone (=posterior point of the foramen magnum) 51 and the left and right supra-orbital ridge 52.

Figure 4A:
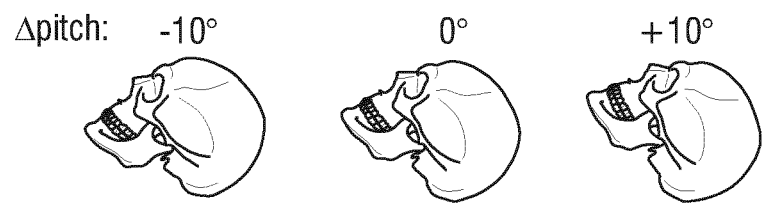
FIGS. 4A-4C show different diagrams illustrating the deviation of the scan FOV from an optimal FOV with respect to the different parameters.
Figure 4B:
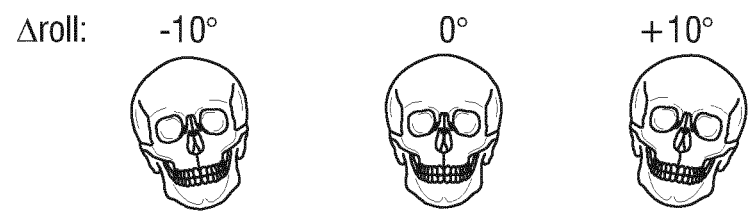
Figure 4C:
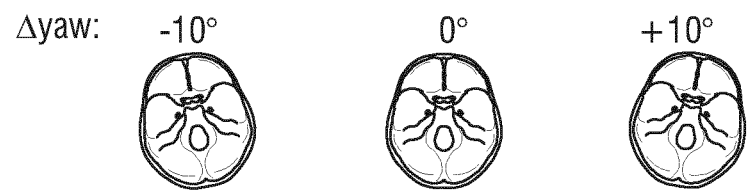

The deviation of the actual scan volume and the optimal scan volume is computed and may be separated into four different parameters: $\Delta z$ denoting the deviation of the inferior extent of the scan volume, wherein positive $\Delta z$ indicates that the scan was continued further down than required. $\Delta$pitch, $\Delta$roll, and $\Delta$yaw denote the deviation from the optimal scan with respect to the three angular components as shown in FIGS. 4A-4C.

Figure 5:
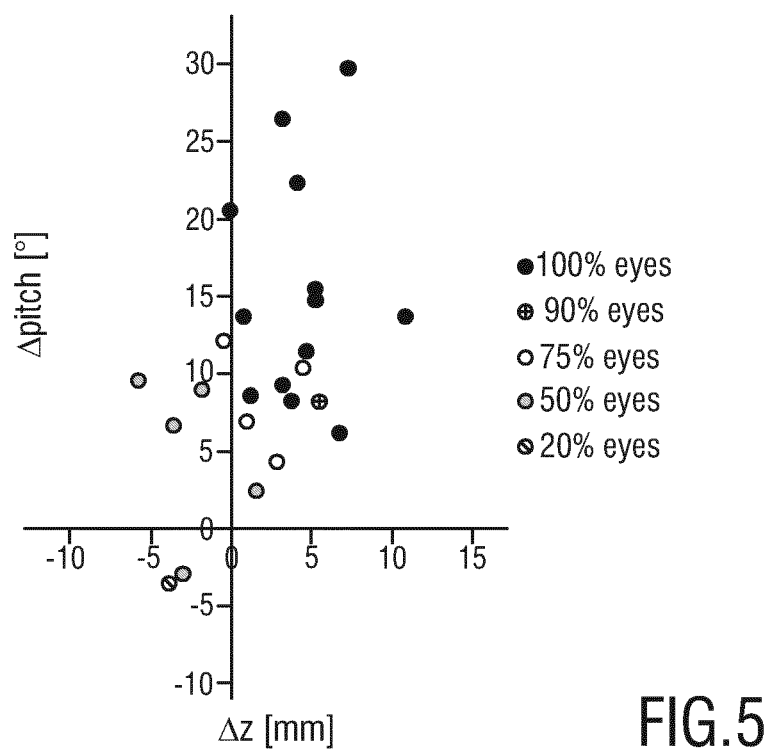
FIG. 5 shows a diagram illustrating the correlation of error sources to the image quality in terms of percentage of eyes within the field of view.

The error parameters are linked to different root-causes as illustrated in FIG. 5 showing a diagram illustrating the correlation of error sources to the image quality in terms of percentage of eyes within the field of view. These root-causes may include one or more of:

A large $\Delta z$ caused during placement of the scan box on the scanner console based on the topogram.

Large deviations in pitch, roll and yaw can be caused by wrong positioning of the patient's head.

In cases where the scanner allows for a tilt of the gantry, a deviation in pitch can either be compensated by better patient positioning, or by adaptation of the gantry tilt.

Having applied the described steps to a large number of image datasets correlations of specific errors with scan boundary conditions will be analyzed. These boundary conditions can include one or more of operator, patient age, reason for scan, patient consciousness and cooperation, time of day, day of the week, etc.

Combining this analysis with the identified root causes will be used in order to propose targeted improvement actions, thus saving time and money by offering efficient training for the staff, where it is most needed. Examples for such proposed improvements may be:

"On average, operator X was observed to extend the scan greater than the average distance in inferior direction. It is recommended to focus on defining the inferior margin of the planned FOV as closely as possible to the plane defined by the connecting plane between the opisthion and the supra-orbital ridges."

"Operator X should team up with operator Y (presenting optimal FOV placement)."

"During the night shift special attention should be put on correct positioning of the head."

Hence, by use of the present invention an automatic quality assessment of medical image datasets can be made to identify potential errors or deviations that may be avoided in future imaging operations.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for quality assessment of medical image datasets, said device comprising:
a memory that stores a plurality of instructions; and
processor circuitry that couples to the memory and that is configured to execute the plurality of instructions to:
obtain medical image datasets together with respective acquisition information, each medical image dataset being acquired by scanning a field of view, FOV, of an examination object and the respective acquisition information representing information related to the acquisition of the respective medical image dataset;
compare the FOV of an obtained medical image dataset with a reference FOV that excludes a predetermined anatomical region;
determine difference information indicating deviations of the FOV from the reference FOV;
determine correlation information indicating correlations between the difference information determined for a plurality of obtained medical image datasets and the respective acquisition information; and
issue the determined correlation information.

2. The device as claimed in claim 1,
wherein the processor circuitry is further configured to determine the reference FOV for comparison with the FOV of an obtained medical image dataset from said medical image dataset.

3. The device as claimed in claim 1,
wherein the processor circuitry is further configured to determine the reference FOV, one or more borders of the reference FOV, by use of anatomical landmarks within the obtained medical image dataset.

4. The device as claimed in claim 1,
wherein the processor circuitry is further configured to determine the reference FOV such that predetermined one or more sensitive organs are excluded from the reference FOV.

5. The device as claimed in claim 1,
wherein the processor circuitry is further configured to obtain the reference FOV for comparison with the FOV of an obtained medical image dataset from a database, an anatomical atlas, based on said medical image dataset.

6. The device as claimed in claim 1,
wherein the processor circuitry is further configured to determine difference information indicating deviations of the FOV from the reference FOV with respect to a predetermined condition, a predetermined anatomical region.

7. The device as claimed in claim 1,
wherein the processor circuitry is further configured to determine first if an obtained medical image dataset complies with a predetermined condition, if it contains a predetermined anatomical region, and to compare the FOV of an obtained medical image dataset with a reference FOV and to determine difference information for an obtained medical image dataset only if it has been determined that the obtained medical image dataset complies with a predetermined condition.

8. The device as claimed in claim 1,
wherein the processor circuitry is further configured to determine difference information comprising translational information indicating deviations in size and/or one or more borders of the FOV of an obtained medical image dataset with respect to a reference FOV.

9. The device as claimed in claim 1,
wherein the processor circuitry is further configured to determine difference information comprising rotational information indicating deviations of the FOV of an obtained medical image dataset with respect to a reference FOV in one or more rotational directions around one or more different rotational axes.

10. The device as claimed in claim 1,
wherein the processor circuitry is further configured to determine difference information comprising presence information indicating the extent of presence of a predetermined anatomical region, one or more sensitive organs, in the FOV of an obtained medical image dataset.

11. The device as claimed in claim 1, wherein said acquisition information comprises at least one of:
temporal information indicating the time, the day of the week and the time of day, of the acquisition of the respective medical image dataset,
object information indicating the condition of the imaged examination object,
position information indicating the position of the examination object with respect to an imaging device by which the respective medical image dataset has been acquired, and
operator information about the operator indicating the operator who carried out the acquisition of respective medical image dataset.

12. The device as claimed in claim 3,
wherein said medical image datasets are CT image datasets, of a human head, and
wherein said predetermined anatomical region includes eyes and said anatomical landmarks are left and right supra orbital ridges an opisthion of an occipital bone.

13. An imaging system comprising
an image acquisition system acquiring medical image datasets of examination objects, and
a device as claimed in claim 1 for quality assessment of the acquired medical image datasets.

14. A method for quality assessment of medical image datasets, said method comprising:
obtaining medical image datasets together with respective acquisition information, each medical image dataset being acquired by scanning a field of view, FOV, of an examination object and the respective acquisition information representing information related to the acquisition of the respective medical image dataset;
comparing the FOV of an obtained medical image dataset with a reference FOV that excludes a predetermined anatomical region;
determining difference information indicating deviations of the FOV from the reference FOV;
determining correlation information indicating correlations between the difference information determined for a plurality of obtained medical image datasets and the respective acquisition information; and
issuing the determined correlation information.

15. A non-transitory computer-readable medium having one or more executable instructions stored thereon which, when executed by at least one processor, cause the at least one processor to perform a method for quality assessment of medical image datasets, said method comprising:
- obtaining medical image datasets together with respective acquisition information, each medical image dataset being acquired by scanning a field of view, FOV, of an examination object and the respective acquisition information representing information related to the acquisition of the respective medical image dataset;
- comparing the FOV of an obtained medical image dataset with a reference FOV that excludes a predetermined anatomical region;
- determining difference information indicating deviations of the FOV from the reference FOV;
- determining correlation information indicating correlations between the difference information determined for a plurality of obtained medical image datasets and the respective acquisition information; and
- issuing the determined correlation information.

* * * * *